United States Patent
Sasse et al.

(10) Patent No.: US 7,045,633 B2
(45) Date of Patent: *May 16, 2006

(54) HYDRATE OF 5-[4-[2-(N-METHYL-N-(2-PYRIDIL) AMINO)ETHOXY]BENZYL] THIAZOLIDINE-2,4-DIONE MALEIC ACID SALT

(75) Inventors: Michael John Sasse, Tunbridge Wells (GB); Paul David James Blackler, Tonbridge (GB); David C Lee, Linton (GB)

(73) Assignee: SmithKline Beecham PLC, Brentford (GB)

( * ) Notice: Subject to any disclaimer, the term of this patent is extended or adjusted under 35 U.S.C. 154(b) by 1 day.

This patent is subject to a terminal disclaimer.

(21) Appl. No.: 10/692,544

(22) Filed: Oct. 24, 2003

(65) Prior Publication Data
US 2004/0097553 A1    May 20, 2004

Related U.S. Application Data

(63) Continuation of application No. 10/072,096, filed on Feb. 7, 2002, now Pat. No. 6,664,278, which is a continuation of application No. 09/581,719, filed as application No. PCT/EP98/08154 on Dec. 14, 1998, now abandoned.

(30) Foreign Application Priority Data

Dec. 16, 1997 (GB) ................................. 9726568.0

(51) Int. Cl.
  *C07D 417/12* (2006.01)
(52) U.S. Cl. ................................. 546/269.7
(58) Field of Classification Search ............. 546/269.7
  See application file for complete search history.

(56) References Cited

U.S. PATENT DOCUMENTS

| 5,002,953 A | 3/1991 | Hindley ...................... 514/275 |
| 5,741,803 A | 4/1998 | Pool et al. .................. 514/342 |
| 5,910,592 A | 6/1999 | Pool et al. ................ 546/269.7 |
| 6,664,278 B1 * | 12/2003 | Sasse et al. ................. 514/342 |
| 2002/0133016 A1 | 9/2002 | Lynch et al. ............. 546/269.7 |
| 2002/0137940 A1 | 9/2002 | Sasse et al. ............. 546/269.7 |

FOREIGN PATENT DOCUMENTS

| EP | 0 306 228 A1 | 8/1989 |
| EP | 0 306 228 B1 | 11/1999 |
| WO | WO 93/10254 | 3/1993 |
| WO | WO 94/05659 | 3/1994 |
| WO | WO 94/05669 | 3/1994 |
| WO | WO 95/21603 | 8/1995 |
| WO | WO 99/31093 | 6/1999 |
| WO | WO 99/31095 | 6/1999 |
| WO | WO 00/64892 | 11/2000 |
| WO | WO 00/64893 | 11/2000 |
| WO | WO 00/64896 | 11/2000 |

OTHER PUBLICATIONS

Cantello, et al., "The Synthesis of BRL 49653—A Novel and Potent Antihyperglycaemic Agent". *Bioorganic & Medicinal Chemistry Letters*, 4(10): 1181-1184 (1994).

Haleblian, et al., "Pharmaceutical Applications of Polymorphism". *Journal of Pharmaceutical Sciences*, 58(8): 911-929 (1969).

Cantello, et al., "Facile Biocatalytic Reduction of the Carbon—Carbon Double Bond of 5-Benzylidenethiazolidine-2,4-diones. Synthesis of (+)-5-(4-[2-Methyl(2-pyridyl)amino]ethoxy benzyl)thiazolidine-2,4-dione (BRL 49653), its (R)-(+)-Enantiomer and Analogues". *J. Chem. Soc, Perkin Transactions 1*, pp. 3319-3324 (1994).

* cited by examiner

*Primary Examiner*—Zinna N. Davis
(74) *Attorney, Agent, or Firm*—Kathryn L. Sieburth; Mary E. McCarthy; Charles M. Kinzig

(57) ABSTRACT

A hydrate of 5-[4-[2-(N-methyl-N-(2-pyridyl)amino) ethoxy]benzyl]thiazolidine-2,4-dione, maleic acid salt, characterized in that it: (i) comprises water in the range of from 0.2 to 1.1% w/w; and (ii) provides an infrared spectrum containing peaks at 764 and 579 $cm^{-1}$; and/or (iii) provides an X-ray powder diffraction (XRPD) pattern substantially as set out in FIG. II; a process for the preparation of such a compound, a pharmaceutical composition containing such a compound and the use of such a compound or composition in medicine.

6 Claims, 2 Drawing Sheets

Figure 1:
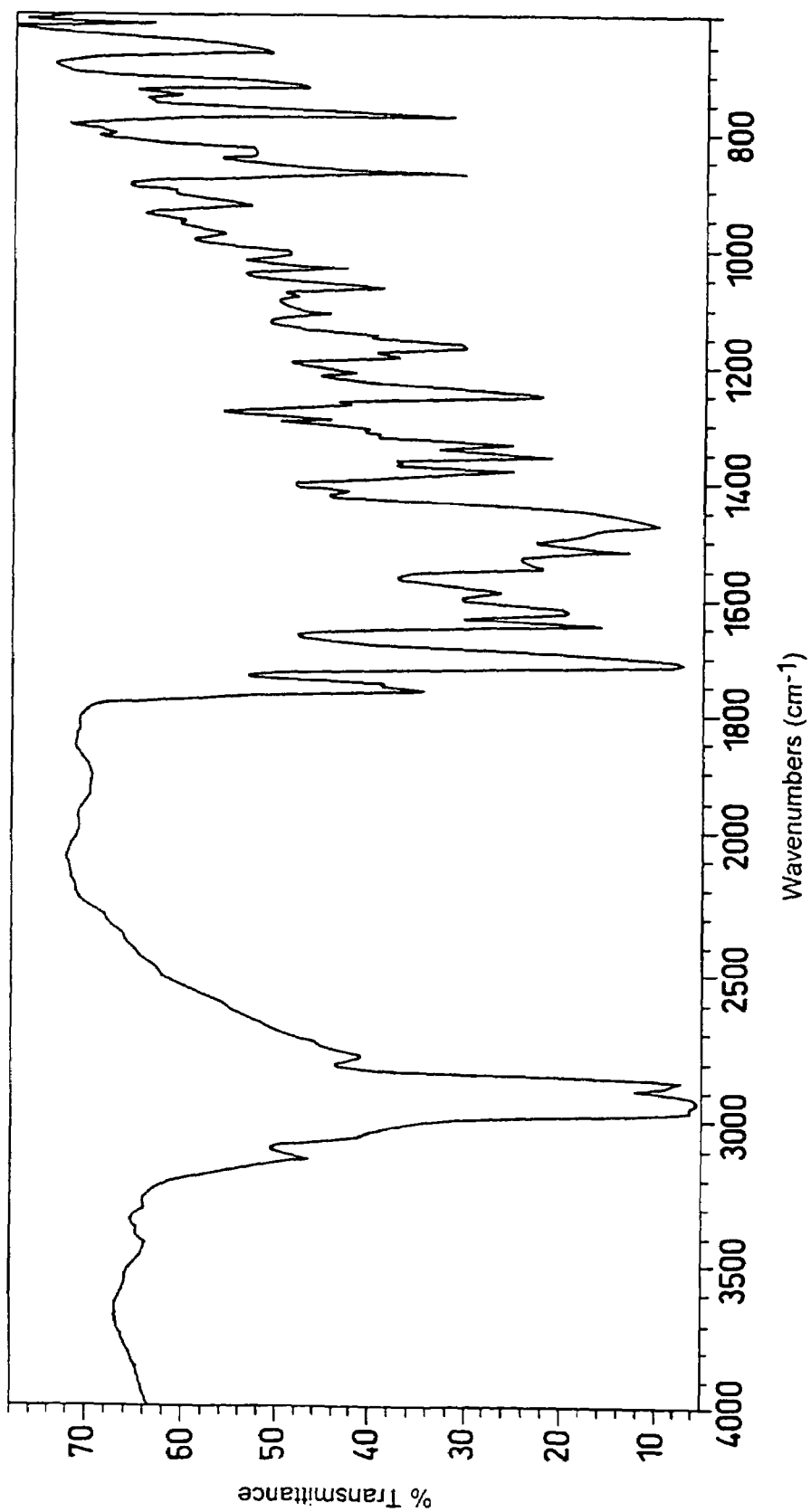
Figure 2:
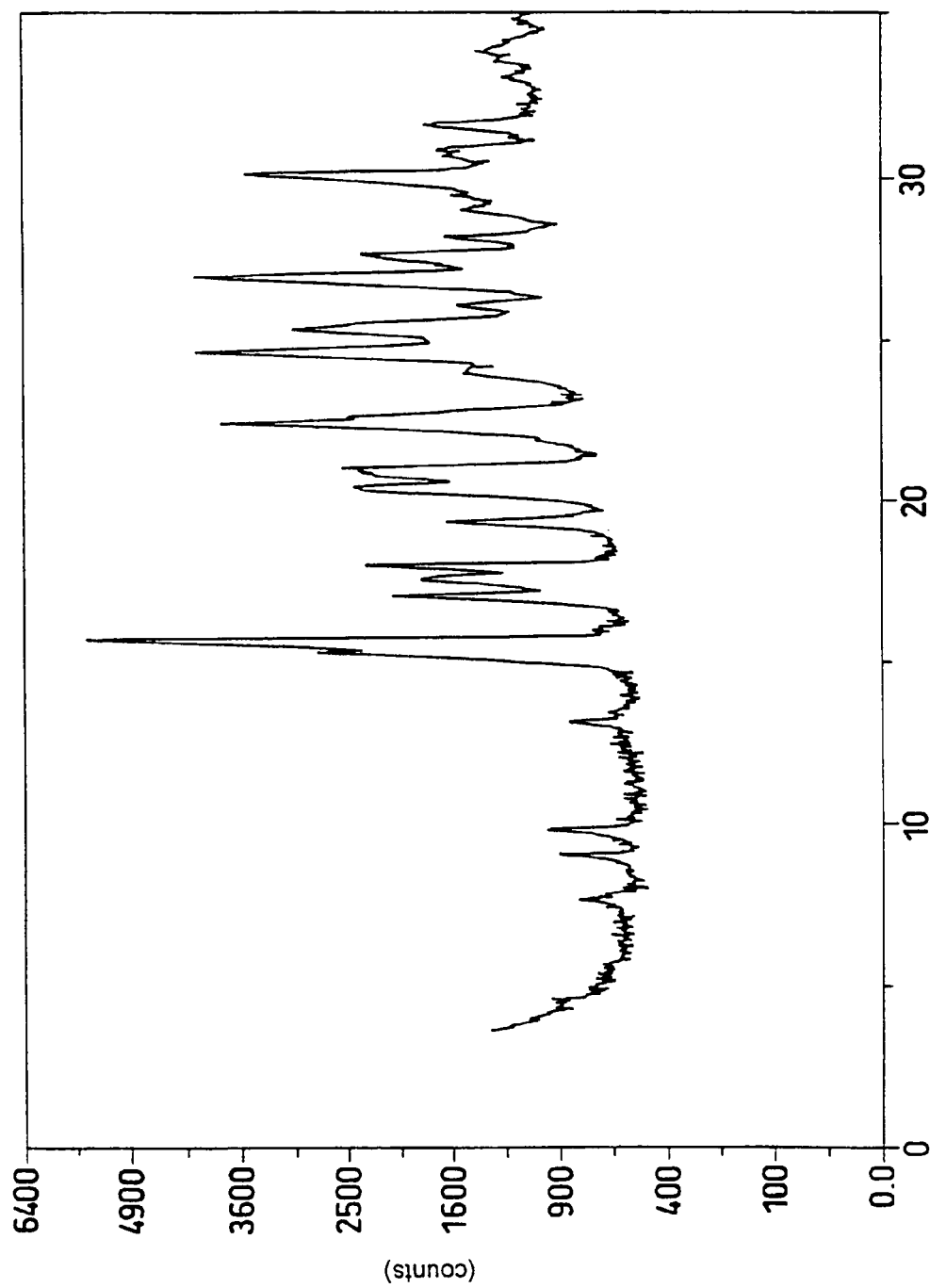

HYDRATE OF 5-[4-[2-(N-METHYL-N-(2-PYRIDIL) AMINO)ETHOXY]BENZYL] THIAZOLIDINE-2,4-DIONE MALEIC ACID SALT

This application is a continuation of Application Ser. No. 10/072,096, filed Feb. 7, 2002. now U.S. Pat. No. 6,664,278, which is a continuation of Application Ser. No. 09/581,7 19, filed Jun. 16, 2000, now abandoned, which is a 371 of International Application No. PCT/EP 98/08154, filed Dec. 14, 1998.

This invention relates to a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl)amino)ethoxy]benzyl] thiazolidine-2,4-dione, maleic acid salt (hereinafter also referred to as "Compound (I)").

Compound (I) is disclosed solely as an anhydrous form. It has now been discovered that Compound (I) exists in a novel hydrated form which is particularly suitable for bulk preparation and handling. This can be prepared by an efficient, economic and reproducible process particularly suited to large scale preparation.

The novel hydrate also has useful pharmaceutical properties and in particular it is indicated to be useful for the treatment and/or prophylaxis of diabetes mellitus, conditions associated with diabetes mellitus and certain complications thereof.

Accordingly, the present invention provides a hydrate of 5-[4-[2-(N-methyl-N-(2-pyridyl)amino)ethoxy]benzyl]thiazolidine-2,4-dione, maleic acid salt (the "Hydrate") characterised in that the Hydrate:
(i) comprises water in the range of from 0.2 to 1.1% w/w; and
(ii) provides an infra red spectrum containing peaks at 764 and 579 $cm^{-1}$; and/or
(iii) provides an X-ray powder diffraction (XRPD) pattern substantially as set out in FIG. II.

Suitably, the water content of the Hydrate is in the range of from 0.4 to 0.9% w/w, especially 0.5 to 0.6% w/w, for example 0.54% w/w or 0.6% w/w.

In one favoured aspect, the Hydrate provides an infra red spectrum substantially as set out in accordance with FIG. I.

The Hydrate can exist in certain dehydrated forms which reversibly convert to the Hydrate when contacted with water, either in liquid or vapour form. The present invention encompasses all such reversibly rehydratable forms of the Hydrate.

The present invention encompasses the Hydrate isolated in pure form or when admixed with other materials, for example the known anhydrous form of Compound I, the above mentioned reversibly rehydratable forms or any other material.

Thus in one aspect there is provided the Hydrate in isolated form.

In a further aspect there is provided the Hydrate in pure form.

In yet a further aspect there is provided the Hydrate in crystalline form.

The invention also provides a process for preparing the Hydrate, characterised in that 5-[4-[2-(N-methyl-N-(2-pyridyl)amino)ethoxy]benzyl]thiazolidine-2,4-dione, maleic acid salt is crystallised from an aqueous alkanolic solvent, preferably containing from 2.0 to 2.5% by volume of water, most preferably 2.0 to 2.3%, for example 2.1% by volume of water.

Suitable aqueous alkanolic solvents include aqueous ethanol, typically aqueous denatured ethanol, and aqueous isopropanol, or mixtures thereof.

Crystallisation and any recrystallisation is generally carried out at low to ambient temperature, such as in the range of between 0 to 30° C. for example 25° C.; alternatively crystallisation may be initiated at an elevated temperature, such as in the range of between 30° C. and 60° C. for example 35° C., and then completed by allowing the temperature of the solvent to cool to ambient or low temperature, such as in the range of between 0 to 30° C. for example 25° C.

The crystallisation can be initiated by seeding with crystals of the Hydrate but this is not essential.

Compound I is prepared according to known procedures, such as those disclosed in WO94/05659. The disclosures of WO94/05659 are incorporated herein by reference.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance, especially acquired insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As used herein 'aqueous' with reference to a given solvent or solvent mixture refers to a solvent which contains sufficient water to provide Hydrate i.e having from 0.2 to 1.1% w/w of water.

As mentioned above the compound of the invention has useful therapeutic properties: The present invention accordingly the Hydrate for use as an active therapeutic substance.

More particularly, the present invention provides the Hydrate for use in the treatment and/or prophylaxis of diabetes mellitus, conditions associated with diabetes mellitus and certain complications thereof.

The Hydrate may be administered per se or, preferably, as a pharmaceutical composition also comprising a pharmaceutically acceptable carrier. The formulation of the Hydrate and dosages thereof are generally as disclosed for Compound (I) in International Patent Application, Publication Number WO94/05659.

Accordingly, the present invention also provides a pharmaceutical composition comprising the Hydrate and a pharmaceutically acceptable carrier therefor.

The Hydrate is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents ,lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

As is common practice, the compositions will usually be accompanied by written or printed directions for use in the medical treatment concerned.

As used herein the term 'pharmaceutically acceptable' embraces compounds, compositions and ingredients for both human and veterinary use. for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of Hydrate to a human or non-human mammal in need thereof.

Conveniently, the active ingredient may be administered as a pharmaceutical composition hereinbefore defined, and this forms a particular aspect of the present invention.

In the treatment and/or prophylaxis of diabetes mellitus, conditions associated with diabetes mellitus and certain complications thereof Hydrate may be taken in doses, such as those described above.

Similar dosage regimens are suitable for the treatment and/or prophylaxis of non-human mammals.

In a further aspect the present invention provides the use of Hydrate for the manufacture of a medicament for the treatment and/or prophylaxis of diabetes mellitus, conditions associated with diabetes mellitus and certain complications thereof.

No adverse toxicological effects are indicated for the compounds of the invention in the above mentioned treatments.

The following examples illustrate the invention but do not limit it in any way.

EXAMPLE 1

Preparation of Hydrate of 5-[4-[2-(N-methyl-N-(2pyridyl)amino) thoxy]benzyl]thiazolidine-2,4-dione, Maleic Acid Salt 5-[4-[2-(N-methyl-N-(2-pyridyl)amino)ethoxy]benzyl] thiazolidine-2,4-dione free base (4.0 g) and maleic acid (1.40 g, 1.05 molar equivalents) were heated in denatured ethanol (40 ml) containing additional water (0.51 g, i.e. a total water content of approximately 2.1% (v/v)) to 60° C. and held at this temperature for 30 minutes during which time a solution was obtained. The solution was filtered, re-heated to 50° C., and then cooled with stirring at a rate of 1 deg/min, resulting in crystallisation at 35° C. The resulting suspension was cooled to 25° C. and stirred for two hours. The product was filtered, washed with 99% denatured ethanol (8 ml) and dried at 50° C. in vacuo for 24 hours to give the title compound (4.38 g, 82%). The water content of the product was 0.54% w/w.

Characterising Data:

The following characterising data was generated for the Hydrate:

A Infrared

The infrared absorption spectrum of the Hydrate was obtained using a Nicolet 710 FT-IR spectrometer at 2 cm$^{-1}$ resolution. Data were digitised at 1 cm$^{-1}$ interval. The spectrum obtained is shown in FIG. I. Peak positions are as follows: 3129, 2776, 1756, 1747, 1706, 1641, 1617, 1586, 1542, 1512, 1413, 1351, 1331, 1290, 1264, 1246, 1210, 1182, 1163, 1108, 1078, 1064, 1031, 1005, 975, 955, 926, 865, 764, 738, 719, 662, 619, 579, 557, 532, 525, and 508 cm$^{-1}$.

B X-Ray Powder Diffraction (XRPD)

The XRPD pattern of the Hydrate is shown below in FIG. II and a summary of the XRPD angles and calculated lattice spacing characteristic of the Hydrate is given in Table I.

A PW1710 X-ray powder diffractometer (Cu X-ray source) was used to generate the spectrum using the following acquisition conditions:

| | |
|---|---|
| Tube anode: | Cu |
| Generator tension: | 40 kV |
| Generator current: | 30 mA |
| Start angle: | 3.5° 2θ |
| End angle: | 35.0° 2θ |
| Step size: | 0.020 |
| Time per step: | 4.550 s |

TABLE I

X-Ray Powder Diffraction Angles and Calculated Lattice Spacing Characteristic of the Hydrate.

| Diffraction Angle (° 2θ) | Lattice Spacing (Angstroms) |
|---|---|
| 7.6 | 11.65 |
| 8.9 | 9.90 |
| 9.7 | 9.09 |
| 15.1 | 5.85 |
| 15.6 | 5.68 |
| 17.0 | 5.22 |
| 17.5 | 5.08 |
| 17.9 | 4.96 |
| 19.2 | 4.62 |
| 20.1 | 4.41 |
| 20.6 | 4.30 |
| 22.2 | 4.00 |
| 23.8 | 3.73 |
| 24.4 | 3.64 |
| 25.2 | 3.54 |
| 25.9 | 3.44 |
| 26.7 | 3.34 |
| 27.5 | 3.25 |
| 28.0 | 3.19 |
| 29.9 | 2.99 |
| 31.5 | 2.84 |

The invention claimed is:

1. A process for preparing a compound, which is a hydrate of 5-[4-[2-(N-methyl-N-(2-pyridyl)amino)ethoxy]benzyl]-thiazolidine-2,4-dione, maleic acid salt, said process comprising crystallizing a maleic acid salt of 5-[4-[2-(N-methyl-N-(2-pyridyl)amino)ethoxy]benzyl]thiazolidine-2,4-dione from an aqueous alkanolic solvent selected from the group consisting of aqueous denatured ethanol, aqueous isopropanol and mixtures thereof, wherein said compound contains water in the range of from 0.2 to 1.1 % w/w and said compound provides at least one of:

(i) an infra red spectrum containing peaks at 764 and 579 cm$^{-1}$; and (ii) an X-ray powder diffraction pattern substantially in accordance with FIG. II.

2. A process according to claim 1 wherein the aqueous alkanolic solvent contains from 2% to 2.5% of water by volume.

3. A process according to claim 1 wherein the aqueous alkanolic solvent contains from 2% to 2.3% of water by volume.

4. A process according to claim 1 wherein the aqueous alkanolic solvent contains 2.1% of water by volume.

5. A process according to claim 1 for preparing a compound, which is a hydrate of 5-[4-[2-(N-methyl-N-( 2-pyridyl)amino)ethoxy]benzyl]-thiazolidine-2,4-dione, maleic acid salt, said process comprising crystallizing a maleic acid salt of 5-[4-[2-(N-methyl-N-(2-pyridyl)amino)ethoxy]benzyl]-thiazolidine-2,4-dione from an aqueous alkanolic solvent selected from the group consisting of aqueous denatured ethanol, aqueous isopropanol and mixtures thereof, wherein said compound contains water in the range of from 0.2 to 1.1% w/w and said compound, in a mineral oil dispersion, provides an infra red spectrum substantially in accordance with FIG. I.

6. A process for preparing a compound, which is a hydrate of 5-[4-[2-(N-methyl-N-(2-pyridyl)amino)ethoxybenzyl]-thiazolidine-2,4-dione, maleic acid salt, said process comprising crystallizing a maleic acid salt of 5-[4-[2-(N-methyl-N-(2-pyridyl)amino)ethoxy]benzyl]thiazolidine-2,4-dione from an aqueous alkanolic solvent selected from the group consisting of aqueous denatured ethanol, aqueous isopropanol and mixtures thereof, wherein said compound contains water in the range of from 0.2 to 1.1% w/w and said compound provides an X-ray powder diffraction pattern is substantially in accordance with in FIG. II.

* * * * *